United States Patent [19]  [11]  4,062,961
Kaiser et al.  [45] * Dec. 13, 1977

[54] PHARMACEUTICAL COMPOSITIONS AND METHODS OF INHIBITING PHENYLETHANOLAMINE N-METHYLTRANSFERASE

[75] Inventors: Carl Kaiser, Haddon Heights, N.J.; Robert G. Pendleton, Philadelphia, Pa.

[73] Assignee: SmithKline Corporation, Philadelphia, Pa.

[*] Notice: The portion of the term of this patent subsequent to Oct. 26, 1993, has been disclaimed.

[21] Appl. No.: 712,125

[22] Filed: Aug. 5, 1976

Related U.S. Application Data

[60] Division of Ser. No. 590,772, June 26, 1975, Pat. No. 3,988,339, which is a continuation-in-part of Ser. No. 440,925, Feb. 8, 1974, Pat. No. 3,939,164.

[51] Int. Cl.$^2$ .............................................. A61K 31/47
[52] U.S. Cl. .................................................... 424/258
[58] Field of Search ........................................ 424/258

[56] References Cited
U.S. PATENT DOCUMENTS
3,988,339  10/1976  Kaiser et al. .......................... 424/258

Primary Examiner—Stanley J. Friedman
Attorney, Agent, or Firm—Joan S. Keps; Richard D. Foggio; William H. Edgerton

[57] ABSTRACT

Pharmaceutical compositions and methods of inhibiting phenylethanolamine N-methyltransferase using 7 and-/or 8 substituted 1,2,3,4-tetrahydroisoquinoline compounds.

8 Claims, No Drawings

PHARMACEUTICAL COMPOSITIONS AND METHODS OF INHIBITING PHENYLETHANOLAMINE N-METHYLTRANSFERASE

This is a division of application Ser. No. 590,772 filed June 26, 1975, now U.S. Pat. No. 3,988,339 which is a continuation-in-part of now U.S. Pat. No. 3,939,164.

This invention relates to new pharmaceutical compositions and methods of inhibiting phenylethanolamine N-methyltransferase with 1,2,3,4-tetrahydroisoquinoline compounds having substituents in the 7 and/or 8 positions.

Epinephrine is a hormone, synthesized in the adrenal medulla, which is released into the blood stream in response to stress and produces profound physiological changes which serve to prepare the animal to cope with the stressor situation. For example, epinephrine produces anxiety, an increase in blood pressure, acceleration of heart rate and increase in cardiac output. These changes are detrimental in individuals with certain disease conditions such as angina pectoris, myocardial infarction and anxiety neuroses. Epinephrine is also synthesized and released from neuronal sites within the central nervous system and functions in the control of blood pressure and heart rate.

The enzyme phenylethanolamine N-methyltransferase catalyzes the final step in the biosynthesis of epinephrine, that is the transfer of a methyl group from S-adenosy-L-methionine to norepinephrine to produce epinephrine.

The 1,2,3,4-tetrahydroisoquinoline compounds of the pharmaceutical compositions and methods of this invention inhibit phenylethanolamine N-methyltransferase and thus reduce the formation of epinephrine. They are therefore useful in situation where there is overproduction of epinephrine or where epinephrine production is detrimental.

These compounds also produce a reduction in blood pressure and heart rate and are useful as hypotensive agents. This invention also relates to a method of producing hypotensive activity by administering these compounds.

The 1,2,3,4-tetrahydroisoquinoline compounds which are the active ingredients of the pharmaceutical compositions of this invention and are used in the methods of this invention are represented by the following formula:

Formula I

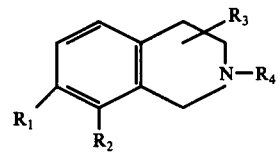

in which:

$R_1$ and $R_2$ are hydrogen, chloro, bromo, fluoro, iodo, trifluoromethyl, amino, lower alkyl, sulfamoyl, methylsulfamoyl, dimethylsulfamoyl or nitro, provided that $R_1$ and $R_2$ are not both hydrogen and provided that when one of $R_1$ and $R_2$ is amino or lower alkyl, the other is not hydrogen, amino or lower alkyl and $R_3$ and $R_4$ are hydrogen, methyl or ethyl or a pharmaceutically acceptable, acid addition salt thereof.

The compounds of Formula I as referred to herein include the pharmaceutically acceptable acid addition salts of the 1,2,3,4-tetrahydroisoquinoline compounds.

In preferred pharmaceutical compositions and methods of this invention the active ingredient is a compound of Formula I in which $R_1$ and $R_2$ are hydrogen, chloro, trifluoromethyl, amino, methyl, sulfamoyl, methylsulfamoyl, dimethylsulfamoyl or nitro, provided that $R_1$ and $R_2$ are not both hydrogen and provided that when one of $R_1$ and $R_2$ is amino, methyl or nitro, the other is not hydrogen, amino, methyl or nitro; and $R_3$ and $R_4$ are hydrogen or methyl. Most preferably $R_1$ and $R_2$ are chloro.

A particularly preferred compound in the pharmaceutical compositions and methods of this invention is 7,8-dichloro-1,2,3,4-tetrahydroisoquinoline hydrochloride.

Some of the 1,2,3,4-tetrahydroisoquinoline compounds of Formula I are known to the art, for example, 7-chloro, 7-bromo, 7-fluoro and 7-iodo 1,2,3,4-tetrahydroisoquinoline are reported in U.S. Pat. No. 3,314,963.

The compounds of Formula I are prepared by the following procedures:

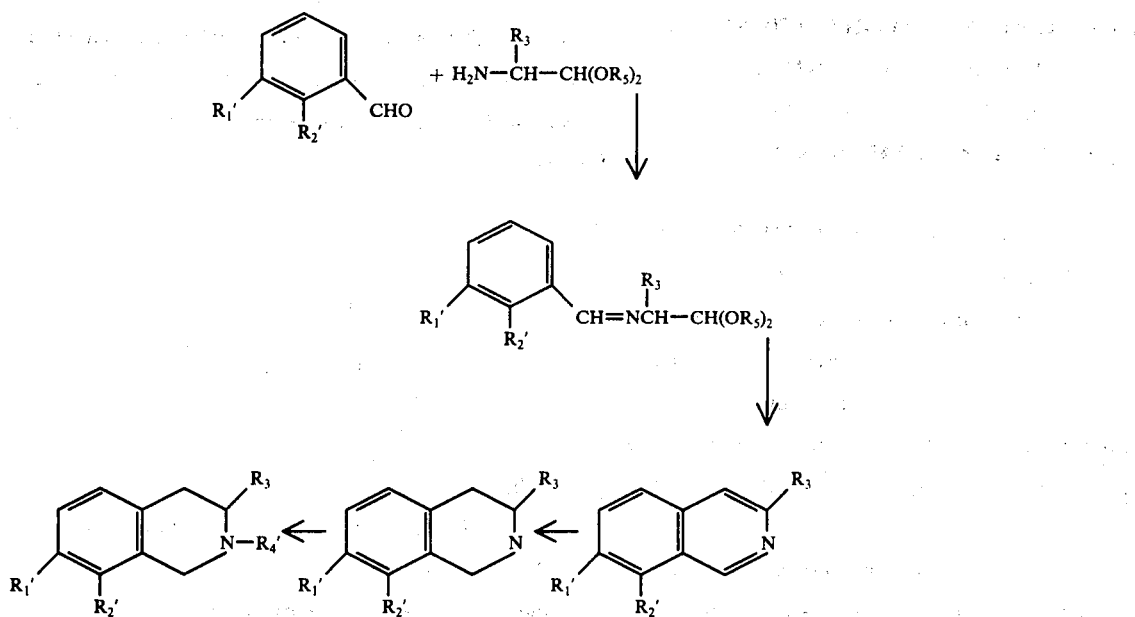

The term $R_3$ is defined above, $R_1'$ and $R_2'$ are hydrogen, chloro, bromo, fluoro, iodo, trifluoromethyl or lower alkyl, $R_5$ is methyl or ethyl and $R_4'$ is methyl or ethyl.

According to the above procedure, isoquinolines are prepared by the Pomeranz-Fritsch reaction; that is, by the reaction of a benzaldehyde with a 2,2-di-lower alkoxyethylamine and acid-catalyzed cyclization of the resulting 2,2-di-lower alkoxy-N-benzylidene-ethylamine. The benzaldehyde and the 2,2-di-lower alkoxyethylamine are preferably reacted in an organic solvent such as toluene at elevated temperature, for example at reflux temperature. The cyclization is carried out with an acid catalyst such as sulfuric acid and phosphorus pentoxide or in sulfuric acid alone. When $R_2$ is hydrogen, isomers may result from the cyclization, that is the 5-$R_1$ as well as the 7-$R_1$ isoquinoline may be formed. The 7-$R_1$ isoquinoline may be separated from the other isomer by standard procedures, for example by chromatography.

The isoquinolines are hydrogenated using a hydrogenation catalyst such as platinum dioxide to give the N-unsubstituted- 1,2,3,4-tetrahydroisoquinolines of the pharmaceutical compositions and methods of this invention.

The N-methyl and ethyl tetrahydroisoquinolines are prepared from the N-unsubstituted compounds by conventional alkylation procedures, for example by treating with formaldehyde and formic acid to give the N-methyl compounds or by treating with a formyl or acetyl halide and reducing the resulting N-acyl compound with diborane to give the N-methyl and N-ethyl compounds.

Alternatively, the N-substituted tetrahydroisoquinolines are prepared by alkylating the isoquinolines by standard procedures, for example by treating them with methyl or ethyl iodide, then reducing the resulting methiodide or ethiodide, for example with sodium borohydride, to give the N-methyl and N-ethyl tetrahydroisoquinolines.

Other of the $R_1$ and $R_2$ substituted tetrahydroisoquinolines are prepared from known isoquinolines by conventional chemical procedures for introducing amino, sulfamoyl, methylsulfamoyl and dimethylsulfamoyl groups. For example, an amino group may be introduced by reducing a nitro group and the sulfamoyl, methylsulfamoyl and dimethylsulfamoyl groups may be introduced by diazotizing a 7- or 8-amino-2-acetyl-1,2,3,4-tetrahydroisoquinoline compound, then treating with sulfur dioxide and cuprous chloride in acetic acid and reacting the resulting chlorosulfonyl substituted isoquinoline with ammonia, methylamine or dimethylamine, followed by acid hydrolysis of the acetyl group. The nitro compounds are obtained by diazotizing an amino substituted isoquinoline and treating with sodium nitrite and calcium carbonate or by oxidation of an amino-2-acetyl-1,2,3,4-tetrahydroisoquinoline with a peracid.

The 4-alkyl compounds of Formula I are prepared by acid cyclization of an N-formyl-$\beta$-alkylphenethylamine and then hydrogenating to give the 4-alkyl-1,2,3,4-tetrahydroisoquinoline.

The pharmaceutically acceptable, acid addition salts of the compounds of Formula I are formed with organic and inorganic acids by methods known to the art. The base is reacted with an organic or inorganic acid in aqueous miscible solvent, such as acetone or ethanol, with isolation of the salt by concentration and cooling or in aqueous immiscible solvent, such as ethyl ether or chloroform, with the desired salt separating directly. Exemplary of the salts which are included in this invention are maleate, fumarate, benzoate, ascorbate, pamoate, succinate, bismethylenesalicylate, methanesulfonate, ethanedisulfonate, benzenesulfonate, acetate, propionate, tartrate, salicylate, citrate, gluconate, lactate, mandelate, cinnamate, citraconate, aspartate, stearate, palmitate, itaconate, glycolate, p-aminobenzoate, glutamate, theophylline acetates, hydrochloride, hydrobromide, sulfate, cyclohexylsulfamate, phosphate and nitrate salts.

The activity of the compounds in Formula I is demonstrated by inhibition of phenylethanolamine N-methyltransferase in vitro, by the assay procedure described by Pendleton and Snow, Molecular Pharmacology 9:718–725 (1973), at concentrations of about 1 to 20 × $10^{-7}$ M. For example, at a concentration of 1.2 × $10^{-7}$ M, a preferred compound of the pharmaceutical compositions and methods of this invention 7,8-dichloro-1,2,3,4-tetrahydroisoquinoline inhibits phenylethanolamine N-methyltransferase by 50%.

In addition, the activity of the compounds of Formula I is demonstrated by administration to rats and squirrel monkeys at doses of about 5 to about 100 mg./kg. orally to produce reduction in the conversion rate of norepinephrine to epinephrine in the adrenal glands and in some cases also a reduction in the epinephrine/norepinephrine ratio. These procedures are described by Pendleton et al., *J. Pharmacol. Exp. Therap.* 190:551–562 (1974).

The pharmaceutical compositions of this invention to inhibit phenylethanolamine N-methyltransferase comprise a pharmaceutical carrier and, as the active ingredient, a 1,2,3,4-tetrahydroisoquinoline compound of Formula I. The active ingredient will be present in the compositions of this invention in an effective amount to inhibit phenylethanolamine N-methyltransferase.

Preferably, the compositions of this invention contain the active ingredient of Formula I in an amount of from about 50 mg. to about 1000 mg., advantageously from about 100 mg. to about 500 mg., per dosage unit.

The pharmaceutical carrier may be for example a solid or a liquid. Exemplary of solid carriers are lactose, magnesium stearate, terra alba, sucrose, talc, stearic acid, gelatin, agar, pectin or acacia. The amount of solid carrier will vary widely but preferably will be from about 25 mg. to about 1 gm. Exemplary of liquid carriers are syrup, peanut oil, olive oil, sesame oil, propylene glycol, polyethylene glycol (mol. wt. 200–400) and water. The carrier or diluent may include a time delay material well known to the art such as, for example, glyceryl monostearate or glycerly distearate alone or with a wax.

A wide variety of pharmaceutical forms can be employed, for example the preparation may take the form of tablets, capsules, powders, troches, lozenges, syrups, emulsions, sterile injectable liquids or liquid suspensions or solutions.

The pharmaceutical compositions are prepared by conventional techniques involving procedures such as mixing, granulating and compressing or dissolving the ingredients as appropriate to the desired preparation.

The method of inhibiting phenylethanolamine N-methyltransferase, according to this invention, comprises administering to an animal in an amount sufficient to inhibit phenylethanolamine N-methyltransferase a 1,2,3,4-tetrahydroisoquinoline compound of Formula I. The isoquinoline compound is preferably administered in a dosage unit form.

Preferably, the compounds of Formula I are administered in conventional dosage forms prepared by combining an appropriate dose of the compound with standard pharmaceutical carriers.

Preferably, the active ingredient of Formula I will be administered in a daily dosage regimen of from about 100 mg. to about 2000 mg., most preferably from about 200 mg. to about 1000 mg. Advantageously, equal doses will be administered preferably two to three times per day. When the administration is carried out as described above, inhibition of phenylethanolamin N-methyltransferase is produced.

The route of administration of the pharmaceutical compositions of this invention and in accordance with the methods of this invention is internal, either parenteral or preferably oral, in an amount to produce the desired biological activity.

The following examples are not limiting but are illustrative of this invention.

EXAMPLE 1

A mixture of 65.7 g. (0.375 mole) of 2,3-dichlorobenzaldehyde and 39.4 g. (0.375 mole) of 2,2-dimethoxyethylamine was refluxed azeotropically in 150 cc. of toluene. When all the water was removed (1–2 hours), the solution was concentrated and distilled to give 2,2-dimethoxy-N-(2,3-dichlorobenzylidene)ethylamine, b.p. 140° C. (0.7 mm.).

Ten grams (0.0382 mole) of 2,2-dimethoxy-N-(2,3-dichlorobenzylidene)ethylamine was added dropwise to 100 cc. of concentrated sulfuric acid with stirring at 0–5° C. The solution was added to a mixture of 5 g. of phosphorus pentoxide and 5 cc. of concentrated sulfuric acid. The mixture was stirred and heated at 160° C. for 20 minutes, then cooled to 140° C., maintained there for 20 minutes, then cooled to 100° C. and quenched on ice.

Alternatively and preferably, 10 g. of 2,2-dimethoxy-N-(2,3-dichlorobenzylidene)ethylamine is added dropwise to 120 cc. of concentrated sulfuric acid with stirring at 140° C. The heating is continued for 30 minutes after the addition is complete. While still warm the reaction mixture is poured over ice.

The mixture was then filtered and the filtrate, with cooling, was made basic with 40% aqueous sodium hydroxide solution, then cooled and extracted with ether. The ether was removed from the extract to give 7,8-dichloroisoquinoline as the residue. The 7,8-dichloroisoquinoline was dissolved in acetone. Ethereal hydrogen chloride in slight excess was added to give, after filtering, 7,8-dichloroisoquinoline hydrochloride which after recrystallizing from ethanol melted at 225°–6° C.

The above prepared 7,8-dichloroisoquinoline hydrochloride was reduced in two portions by hydrogenation at 50–60 psi using 0.7 g. of platinum dioxide in 100 cc. of methanol, for one hour at ambient temperature. The mixture was filtered and concentrated. The residue was converted to the base using ammonium hydroxide and was extracted into ether. The extract was dried with magnesium sulfate, filtered and concentrated to give, as the residue, 7,8-dichloro-1,2,3,4-tetrahydroisoquinoline.

The above prepared base was dissolved in about 50 cc. of ethanol. Etheral hydrogen chloride in slight excess was added, then excess ether was added and the solid filtered to give 7,8-dichloro-1,2,3,4-tetrahydroisoquinoline hydrochloride, m.p. 223°–225° C.

If necessary, the 7,8-dichloro-1,2,3,4-tetrahydroisoquinoline can be converted to the N-acetyl compound and crystallized as described in Example 31. The pure N-acetyl derivative is hydrolyzed in refluxing 10% hydrochloric acid, evaporated to dryness in vacuo, and the crystalline residue recrystallized from methanol-ether, m.p. 223°–225° C.

EXAMPLE 2

Bromine (168 g., 1.05 mole) is added over about one hour, with vigorous stirring, to 117.5 g. (0.47 mole) of 2,3-dibromotoluene at 190° C. After the addition is complete, the mixture is cooled to 100° C., then 120 cc. of concentrated sulfuric acid is added and the mixture is stirred for one hour at 100° C. Temperature is raised to 140° C. for five minutes, then the mixture is cooled and the reaction is quenched in ice water. The solid is extracted into ether, and the ether extract is washed with water, then dilute aqueous sodium bicarbonate until the acid is completely removed, and filtered. Removing the ether by evaporation gives 2,3-dibromobenzaldehyde as the residue.

Using 2,3-dibromobenzaldehyde in place of 2,3-dichlorobenzaldehyde in the procedure of Example 1 gives 7,8-dibromo-1,2,3,4-tetrahydroisoquinoline.

EXAMPLE 3

In the procedure of Example 1, using 2,3-difluorobenzaldehyde in place of 2,3-dichlorobenzaldehyde gives, as the product, 7,8-difluoro-1,2,3,4-tetrahydroisoquinoline.

EXAMPLE 4

By the procedure of Example 2, the following halo substituted toluene compounds:
2-bromo-3-chlorotoluene
3-bromo-2-chlorotoluene
2-chloro-3-iodotoluene
3-chloro-2-iodotoluene are converted to the corresponding halo substituted benzaldehydes and these benzaldehydes are used as starting materials in the procedure of Example 1 to give the following products, respectively:
8-bromo-7-chloro-1,2,3,4-tetrahydroisoquinoline
7-bromo-8chloro-1,2,3,4-tetrahydroisoquinoline
8-chloro-7-iodo-1,2,3,4-tetrahydroisoquinoline
7-chloro-8-iodo-1,2,3,4-tetrahydroisoquinoline.

EXAMPLE 5

2,3-Diiodobenzoic acid is treated with diborane in tetrahydrofuran to give 2,3-diiodobenzyl alcohol which is oxidized to 2,3-diiodobenzaldehyde with activated manganese dioxide in methylene chloride.

Using 2,3-diiodobenzaldehyde in place of 2,3-dichlorobenzaldehyde as the starting material in the procedure of Example 1 gives 7,8-diiodo-1,2,3,4-tetrahydroisoquinoline.

EXAMPLE 6

Using 2-bromo-3-iodobenzoic acid as the starting material in the procedure of Example 5 gives 8-bromo-7-iodo-1,2,3,4-tetrahydroisoquinoline.

By the same procedure, using 3-bromo-2-iodobenzoic acid as the starting material, 7-bromo-8-iodo-1,2,3,4-tetrahydroisoquinoline is prepared.

EXAMPLE 7

Using 2,2-diethoxy-1-methylethylamine in place of 2,2,-dimethoxyethylamine in the procedure of Example 1, the product is 7,8-dichloro-3-methyl-1,2,3,4-tetrahydroisoquinoline.

Also, using 1-ethyl-2,2-dimethoxyethylamine, the product is 7,8-dichloro-3-ethyl-1,2,3,4-tetrahydroisoquinoline.

EXAMPLE 8

One gram of 7,8-dichloro-1,2,3,4-tetrahydroisoquinoline is dissolved in ethanol. A molar equivalent amount of maleic acid in ethanol is added. Ether is added and the precipitate is filtered off to give the maleate salt of 7,8-dichloro-1,2,3,4-tetrahydroisoquinoline.

By the same procedure, using citric acid, the citrate salt is prepared.

Reacting one gram of 7,8-dichloro-1,2,3,4-tetrahydroisoquinoline in ethanol with a molar equivalent amount of stearic acid, then adding water and filtering gives the stearate salt.

EXAMPLE 9

2-Chloro-3-methylbenzoic acid was reduced by treating with diborane in tetrahydrofuran and the resulting 2-chloro-3-methylbenzyl alcohol was oxidized with activated magnesium dioxide in methylene chloride to give 2-chloro-3-methylbenzaldehyde.

8-Chloro-7-methylisoquinoline was prepared from 2-chloro-3-methylbenzaldehyde and 2,2-dimethoxyethylamine by the procedure described in Example 1.

The 8-chloro-7-methylisoquinoline was converted to the hydrochloride by treating with ethereal hydrogen chloride. Platinum dioxide (0.2 g.) in 25 ml. of methanol was reduced with hydrogen. The 8-chloro-7-methylisoquinoline hydrochloride was dissolved in the mixture and reduced with hydrogen at atmospheric pressure. The mixture was filtered, concentrated in vacuo and treated with ether to give, after filtering and recrystallizing from 95% ethanol, 8-chloro-7-methyl-1,2,3,4-tetrahydroisoquinoline hydrochloride, m.p. 253°–255° C.

The above prepared hydrochloride salt in methanol is treated with ammonium hydroxide. Extracting with ether, then drying and concentrating the extract gives 8-chloro-7-methyl-1,2,3,4-tetrahydroisoquinoline.

EXAMPLE 10

A solution of 11.0 g. of 8-chloroisoquinoline hydrochloride in 100 ml. of methanol was hydrogenated at atmospheric pressure over 0.5 g. of platinum dioxide as in Example 9. The mixture was filtered and concentrated to small volume. Ether was added, the mixture was filtered, and the solid recrystallized from ethanol to give 8-chloro-1,2,3,4-tetrahydroisoquinoline hydrochloride, m.p. 236°–238.5° C.

EXAMPLE 11

7-Acetamido-8-chloroisoquinoline hydrochloride (9.1 g.) in methanol was reduced as in Example 9 with hydrogen at atmospheric pressure for six hours with a previously hydrogenated platinum oxide catalyst until the theoretical up-take was reached. The catalyst was filtered and washed with methanol. The methanol solution was evaporated and the residue was treated with acetic anhydride, sodium acetate (equimolar) in acetic acid to give 2-acetyl-7-acetamido-1,2,3,4-tetrahydroisoquinoline which was purified via isopropanol recrystallization. The amide was hydrolyzed in 10% hydrochloric acid for four hours. The solution was evaporated to dryness and the residue was recrystallized from methanol-ether to give 7-amino-8-chloro-1,2,3,4-tetrahydroisoquinoline dihydrochloride, m.p. 296°–298° C.

EXAMPLE 12

A mixture of 9.5 g. of 7-chloro-8-nitroisoquinoline, and 14.4 g. of zinc and 48 ml. of acetic acid in 450 ml. of ethanol and 70 ml. of water is heated on a steam bath for five minutes. The reaction mixture is cooled, made alkaline with aqueous ammonium hydroxide and extracted with ethyl acetate. The ethyl acetate is removed from the extract in vacuo to give, as the residue, 8-amino-7-chloroisoquinoline.

8-Amino-7-chloroisoquinoline is refluxed in excess acetic anhydride for two hours or until the reaction is complete. The mixture is then poured into water, neutralized with 10% aqueous sodium bicarbonate solution and extracted with chloroform. The chloroform extract is washed with water, dried over sodium sulfate and concentrated to give 8-acetamido-7-chloroisoquinoline.

The above prepared isoquinoline in ethanol is treated with ethereal hydrogen chloride to give 8-acetamido-7-chloroisoquinoline hydrochloride.

Platinum oxide (0.1 g.) in methanol is reduced with hydrogen at atmospheric pressure. 8-Acetamido-7-chloroisoquinoline hydrochloride (1.0 g.) is treated as in Example 11 to give 8-amino-7-chloro-1,2,3,4-tetrahydroisoquinoline hydrochloride.

EXAMPLE 13

A mixture of 1.1 g. of 7,8-dichloroisoquinoline, an excess of methyl iodide and 20 ml. of ethanol was stirred at room temperature for two days during which methyl iodide was periodically added. The mixture was then diluted with ether and the precipitate was filtered and recrystallized from methanol-ether to give 7,8-dichloroisoquinoline methiodide.

To 1.52 g. of 7,8-dichloroisoquinoline methiodide in 50 ml. of methanol and 5 ml. of water was added 0.78 g. of sodium borohydride in portions. After the addition was complete, the mixture was refluxed for 1.5 hours, cooled, poured into water and extracted with ethyl acetate. The extract was washed with aqueous sodium chloride solution, dried and concentrated. The residue was treated with excess hydrogen chloride in ethanol. Ether is added and the precipitate is filtered off and recrystallized from methanolether to give 7,8-dichloro-2-methyl-1,2,3,4-tetrahydroisoquinoline hydrochloride, m.p. 254°-255° C.

By the same procedure, using ethyl iodide in place of methyl iodide, the product is 7,8-dichloro-2-ethyl-1,2,3,4-tetrahydroisoquinoline.

EXAMPLE 14

7-Aminoisoquinoline (0.005 mole) in 3 ml. of water and 0.45 ml. of concentrated hydrochloric acid was treated with chloral hydrate (0.0054 mole) in 12 ml. of water, 5.7 g. of sodium sulfate in 7.25 ml. of water and hydroxylamine hydrochloride (15 mmoles) in 5 ml. of water and heated on a steam bath until the product crystallized from solution. The reaction mixture was cooled and the product removed by filtration and dried. The resulting 7-isonitrosoacetamidoisoquinoline was added to excess concentrated sulfuric acid maintained at 90°-95° C. After 30 minutes the reaction mixture was poured onto crushed ice, carefully neutralized with aqueous sodium bicarbonate and extracted several times with ethyl acetate. The extracts were combined, washed, dried over sodium sulfate and evaporated to yield 7-amino-8-glyoxylylisoquinoline lactam.

The lactam (0.0725 mole) in 120 ml. of 5% aqueous sodium hydroxide solution was stirred and treated dropwise with 20 ml. of 30% aqueous hydrogen peroxide. The reaction mixture was adjusted to pH 5 with 10% aqueous hydrochloric acid followed by saturated aqueous sodium bicarbonate solution. 7-Amino-8-carboxyisoquinoline was obtained by filtering, drying and recrystallizing from ethanol.

7-Amino-8-carboxyisoquinoline (0.01 mole) in 14 ml. of 6N hydrochloric acid was cooled to −5° C. and treated with sodium nitrite (0.012 mole) in 4 ml. of water. After twenty minutes, the cold solution was added with stirring to cuprous chloride (0.01 mole) in 2.0 ml. of concentrated hydrochloric acid maintained at −5° C. The mixture was stirred at −5° C. for 45 minutes, at 25° C. for 45 minutes, and at 80° C. for 45 minutes. The reaction mixture was adjusted to pH 3 with aqueous sodium hydroxide and saturated with hydrogen sulfide. The cuprous sulfide formed was filtered, the filtrate was adjusted to pH 5 with saturated aqueous sodium bicarbonate and extracted with n-butanol. The butanol was washed with water, evaporated in vacuo, and the residue taken up in methanol and a small amount of ether and filtered. The filtrate was taken to dryness to give crude 8-carboxy-7-chloroisoquinoline which was recrystallized from methyl ethyl ketone and water.

8-Carboxy-7-chloroisoquinoline (0.27 mole), sulfur tetrafluoride (0.83 mole) and hydrofluoric acid (2.7 moles) are heated in an autoclave with rocking at 150° C. for 16 hours. The mixture is cooled and vented. The residue is treated with aqueous sodium carbonate solution and extracted with ether. The ether is evaporated to yield crude 7-chloro-8-trifluoromethylisoquinoline. The product is dissolved in ether and extracted with hydrochloric acid. The acid extract is made alkaline with aqueous sodium hydroxide and extracted with ether. The ether is removed from the extract in vacuo to give 7-chloro-8-trifluoromethylisoquinoline.

7-Chloro-8-trifluoromethylisoquinoline is converted to the hydrochloride and hydrogenated by the procedure of Example 9 to give 7-chloro-8-trifluoromethyl-1,2,3,4-tetrahydroisoquinoline hydrochloride.

The hydrochloride salt is treated with ammonium hydroxide by the procedure of Example 9 to give 7-chloro-8-trifluoromethyl-1,2,3,4-tetrahydroisoquinoline.

Alternatively, 8-carboxy-7-chloroisoquinoline which is an intermediate in the above procedure may be prepared by the following procedure:

8-Amino-7-chloroisoquinoline (0.026 mole), prepared from 7-chloro-8-nitroisoquinoline by the procedure of Example 12, is stirred in aqueous sulfuric acid at 3° C. and treated with one equivalent of sodium nitrite. The resulting solution is added to a cold mixture of 16 g. of potassium carbonate, 6.6 g. of cuprous cyanide and 11.2 g. of potassium cyanide. The mixture is warmed to 50° C., cooled and extracted with chloroform to yield, after removing the chlorofom from the extract in vacuo, 7-chloro-8-cyanosioquinoline. The material is purified by chromatography on "dry column" alumina eluted with chloroform.

7-Chloro-8-cyanoisoquinoline is mixed with excess hydrochloric acid and heated at 150° C. for eight hours in a sealed tube. The reaction mixture is evaporated to dryness, redissolved in water, treated with a small amount of decolorizing carbon, and the theoretical quantity of ammonia water is added to free the acid. After standing overnight the solid material is filtered off to give 8-carboxy-7-chloroisoquinoline.

EXAMPLE 15

8-Amino-7-chloro-1,2,3,4-tetrahydroisoquinoline, prepared as in Example 12, is treated with one molar equivalent of isopropenyl acetate in refluxing ethyl acetate for 16 hours. The solvent is evaporated and the residue crystallized from benzene to yield 2-acetyl-8-amino-7-chloro-1,2,3,4-tetrahydroisoquinoline.

2-Acetyl-8-amino-7-chloro-1,2,3,4-tetrahydroisoquinoline (0.04 mole) in concentrated hydrochloric acid (8.4 ml.) is cooled to 3° C. and treated with sodium nitrite (0.044 mole) dissolved in water (6 ml.). After stirring for 30 minutes, the reaction is tested for nitrous acid with starch/iodide paper. If the test for nitrous acid is negative, more sodium nitrite is added in small portions with stirring over a period of time until the test is positive. When a positive reaction is obtained, magnesium chloride (0.032 mole) is added and the resulting mixture is added to a mixture of acetic acid (40 ml.) saturated with sulfur dioxide and cuprous chloride dihydrate (0.0129 mole) maintained at 30° C and stirred. After about 30 minutes, the mixture is diluted with water (60 ml.) and extracted with ether. The extract is then washed with dilute aqueous sodium bicarbonate/sodium carbonate solution at pH 8-9, then with water, and dried over sodium sulfate. The ether is evaporated to yield 2-acetyl-8-chlorosulfonyl-7-chloro-1,2,3,4-tetrahydroisoquinoline. 2-Acetyl-8-chlorosulfonyl-7-chloro-1,2,3,4-tetrahydroisoquinoline (0.022 mole) is treated with concentrated ammonium hydroxide (30 ml.) with cooling. The resulting solid is filtered off and washed with water to give 2-acetyl-7-chloro-8-sulfamyl-1,2,3,4-tetrahydroisoquinoline.

2-Acetyl-7-chloro-8-sulfamyl-1,2,3,4-tetrahydroisoquinoline is hydrolyzed in refluxing 10% hydrochloric acid (60 ml.) for 2.5 hours. The reaction mixture is evaporated and the residue treated with methanol and ether. The solid is filtered off to give 7-chloro-8-sulfamoyl-1,2,3,4-tetrahydroisoquinoline hydrochloride. The hydrochloride is treated with ammonium hydroxide as in Example 9 to give 7-chloro-8-sulfamoyl-1,2,3,4-tetrahydroisoquinoline.

EXAMPLE 16

8-Amino-7-chloroisoquinoline (0.005 mole), prepared as in Example 12, in 40% fluoboric acid (30 ml.) is cooled to −10° C. and diazotized with finely powdered sodium nitrite (3.5 g.). After 30 minutes, the reaction mixture is tested for nitrous acid with starch/iodide paper as described in Example 15. When a positive reaction is obtained, the reaction mixture is washed with small portions of ether and then agitated with a mixture of ethanol and ether (20 ml. each). The diazonium tetrafluoroborate is filtered, washed with ether, dried in vacuo and decomposed on an oil bath at approximately 150° C. The residue is partitioned between ether and 5% aqueous sodium hydroxide solution. The ether phase and extracts are combined, washed with water, dried over sodium sulfate and evaporated to yield 7-chloro-8-fluoroisoquinoline.

The 7-chloro-8-fluoroisoquinoline prepared above is converted to 7-chloro-8-fluoro-1,2,3,4-tetrahydroisoquinoline by the procedure of Example 9.

EXAMPLE 17

7-Chloro-8-nitroisoquinoline (0.125 mole) and cuprous cyanide (0.225 mole) are refluxed in 125 ml. of distilled N-methylpyrrolidinone under a nitrogen atmosphere for 16 hours. The reaction mixture is poured into a solution of 40 g. of sodium cyanide in 120 ml. of water. The mixture is cooled and extracted with benzene. The benzene extracts are combined, washed with water, dried over sodium sulfate and evaporated. The residue is recrystallized from benzene to give 7-cyano-8-nitroisoquinoline.

By the procedure of Example 14, the 7-cyano group of 7-cyano-8-nitroisoquinoline is converted to the 7-carboxy group and then to the 7-trifluoromethyl group to give 8-nitro-7-trifluoromethylisoquinoline.

According to the procedure in Example 12, 8-nitro-7-trifluoromethylisoquinoline is heated with zinc and acetic acid in ethanol and water on a steam bath for five minutes and the reaction mixture is cooled, made alkaline with aqueous ammonium hydroxide and extracted with ethyl acetate. Removing the solvent from the extract in vacuo gives, as the residue, 8-amino-7-trifluoromethylisoquinoline.

Hydrogenating the above prepared isoquinoline by the procedure of Example 9 gives 8-amino-7-trifluoromethyl-1,2,3,4-tetrahydroisoquinoline.

EXAMPLE 18

By the procedure of Example 14, 8-amino-7-trifluoromethylisoquinoline is converted to 8-cyano-7-trifluoromethylisoquinoline and that cyano compound is then converted to 8-carboxy-7-trifluoromethylisoquinoline. Then, also by the procedure of Example 14, 8-carboxy-7-trifluoromethylisoquinoline is converted to 7,8-di(trifluoromethyl)isoquinoline.

Hydrogenating 7,8-di(trifluoromethyl)isoquinoline by the procedure of Example 9 gives 7,8-di-(trifluoromethyl)-1,2,3,4-tetrahydroisoquinoline.

EXAMPLE 19

8-Amino-7-trifluoromethylisoquinoline (0.7 g.) in 2 ml. of concentrated hydrochloric acid and 10 ml. of water is diazotized at 0° C. with 0.25 g. of sodium nitrite in 5 ml. of water. The resulting solution is added to a solution of 2 g. of cuprous chloride in 20 ml. of concentrated hydrochloric acid previously warmed to 70° C. After standing overnight, the reaction mixture is basified with 10% aqueous sodium hydroxide solution and extracted with ether. The ether extracts are washed with water, dried over sodium sulfate and evaporated to give 8-chloro-7-trifluoromethylisoquinoline as the residue. This isoquinoline is converted to the hydrochloride and recrystallized from ethanol and ether.

Hydrogenating 8-chloro-7-trifluoromethylisoquinoline hydrochloride by the procedure of Example 9 gives 8-chloro-7-trifluoromethyl-1,2,3,4-tetrahydroisoquinoline.

Alternatively, 8-chloro-7-trifluoromethylisoquinoline is prepared from 7-amino-8-chloroisoquinoline via the 7-cyano and 7-carboxy intermediates by the procedure of Example 14.

Alternatively, the 7-carboxy-8-chlorisoquinoline intermediate may be prepared from 8-aminoisoquinoline by the procedure of Example 14 via the 8-isonitrosoacetamidoisoquinoline, the 7-glyoxylyl-8-aminoisoquinoline lactam intermediate and the 8-amino-7-carboxyisoquinoline intermediate.

EXAMPLE 20

8-Amino-7-trifluoromethyl-1,2,3,4-tretrahydroisoquinoline, prepared as in Example 17, is treated with one molar equivalent of isopropenyl acetate in refluxing ethyl acetate by the procedure of Example 15 to give 2-acetyl-8-amino-7-trifluoromethyl-1,2,3,4-tetrahydroisoquinoline.

The above prepared 8-amino tetrahydroisoquinoline compound is converted to the corresponding 8-chlorosulfonyl compound and then to the 8-sulfamoyl compound, 2-acetyl-8-sulfamoyl-7-trifluoromethyl- 1,2,3,4-tetrahydroisoquinoline, by the procedure of Example 15. The acetyl group is removed by acid hydrolysis by the procedure of Example 15 to give 8-sulfamoyl-7-trifluoromethyl-1,2,3,4-tetrahydroisoquinoline.

EXAMPLE 21

By the procedure of Example 16, 8-amino-7-trifluoromethylisoquinoline is converted to 8-fluoro-7-trifluoromethylisoquinoline. Hydrogenating by the procedure of Example 9 gives 8-fluoro-7-trifluoromethyl-1,2,3,4-tetrahydroisoquinoline.

EXAMPLE 22

By the procedure of Example 15, 7-amino-8-chloro-1,2,3,4-tetrahydroisoquinoline is converted to 8-chloro-7-sulfamoyl-1,2,3,4-tetrahydroisoquinoline.

EXAMPLE 23

Using 7-amino-8-chloroisoquinoline in place of 8-amino-7-chloroisoquinoline in the procedure of Example 16 gives 8-chloro-7-fluoro-1,2,3,4-tetrahydroisoquinoline.

EXAMPLE 24

7-Amino-8-chloroisoquinoline (0.05 mole) in dilute aqueous sulfuric acid at 3° C. is treated with sodium nitrite (0.05 mole). After 30 minutes, the reaction mixture is tested for nitrous acid with starch/iodide paper as described in Example 15. When a positive reaction is obtained, the mixture is neutralized with aqueous calcium carbonate solution and added with stirring to a hot solution (50° C.) of 50 g. of sodium nitrite, 5 g. of cupric sulfate pentahydrate and 50 ml. of water containing 3 g. of cuprous oxide in suspension. The reaction mixture is heated to 70° C. for 10 minutes and then extracted with ether. The extract is evaporated to give 8 chloro-7-nitroisoquinoline. The product is purified by chromatography on silica gel, eluting with ether followed by recrystallization from methanol.

The above prepared 8-chloro compound is converted to 7-nitro-8-trifluoromethylisoquinoline via the 7-cyano and 7-carboxy intermediates by the procedure of Example 17.

Reducing the 7-nitro group of 7-nitro-8-trifluoromethylisoquinoline with zinc and acetic acid by the procedure of Example 17 gives 7-amino-8-trifluoromethylisoquinoline. Hydrogenating by the procedure of Example 9 gives 7-amino-8-trifluoromethyl-1,2,3,4-tetrahydroisoquinoline.

EXAMPLE 25

By the procedure of Example 15, 7-amino-8-trifluoromethyl-1,2,3,4-tetrahydroisoquinoline is converted to 7-sulfamoyl-8-trifluoromethyl-1,2,3,4-tetrahydroisoquinoline.

EXAMPLE 26

By the procedure of Example 16, 7-amino-8-trifluoromethylisoquinoline is converted to 7-fluoro-8-trifluoromethylisoquinoline. This isoquinoline is converted to 7-fluoro-8-trifluoromethyl-1,2,3,4-tetrahydrosioquinoline by the procedure of Example 9.

EXAMPLE 27

2-Acetyl-7-chlorosulfonyl-1,2,3,4-tetrahydroisoquinoline was reacted with a concentrated aqueous solution of methylamine with cooling. The resulting solid was filtered and washed with water to give 2-acetyl-7-methylsulfamoyl-1,2,3,4-tetrahydroisoquinoline. Hydrolyzing in refluxing 10% hydrochloric acid by the procedure of Example 15 and then recrystallizing from methanol/ether gave 7-methylsulfamoyl-1,2,3,4-tetrahydroisoquinoline hydrochloride, m.p. 238°-240° C.

By the same procedure, using dimethylamine in place of methylamine, 7-dimethylsulfamoyl-1,2,3,4-tetrahydroisoquinoline hydrochloride, m.p. 193°-195° C. was prepared.

EXAMPLE 28

8-Aminoisoquinoline is converted to 8-amino-1,2,3,4-tetrahydroisoquinoline by the procedure of Example 9.

By the procedure of Example 15, 8-amino-1,2,3,4-tetrahydroisoquinoline is converted to 2-acetyl-8-chlorosulfonyl-1,2,3,4-tetrahydroisoquinoline. Reacting with metylamine by the procedure of Example 27 and hydrolyzing to remove the 2-acetyl group gives 8-methylsulfamoyl-1,2,3,4-tetrahydroisoquinoline.

Reacting the 8-chlorosulfonyl compound with dimethylamine gives 8-dimethylsulfamoyl-1,2,3,4-tetrahydroisoquinoline.

Example 29

8-Trifluoromethylisoquinoline was prepared from 2-trifluoromethylbenzaldehyde by the procedure of Example 9.

Alternatively, 8-trifluoromethylisoquinoline is prepared by heating 8-carboxyisoquinoline, sulfur tetrafluoride and hydrofluoric acid in an autoclave with rocking at 150° C. for 16 hours and working up as in Example 14.

Converting 8-trifluoromethylisoquinoline to the hydrochloride, m.p. 213°-216.5° C., then treating by the procedure of Example 9 gives 8-trifluoromethyl-1,2,3,4-tetrahydroisoquinoline.

By the same procedure, using 7-carboxyisoquinoline as the starting material, 7-trifluoromethyl-1,2,3,4-tetrahydroisoquinoline is prepared.

EXAMPLE 30

Benzoyl chloride (0.4 mole) is added over three hours to a stirred mixture of potassium cyanide (0.6 mole) in 250 ml. of water and 7,8-dichloroisoquinoline (0.2 mole) maintained at 25° C. The mixture is stirred for one more hour, cooled and filtered. The product is recrystallized from ethanol and dried to yield 2-benzoyl-7,8-dichloro-1-cyano-1,2,-dihydroisoquinoline.

A mixture of the compound prepared above (0.32 mole) in 350 ml. of dioxane and 100 ml. of ether is cooled to −10° C, and a 0.78N ether solution of phenyllithium is added, with stirring, over 30 minutes. Ten minutes after the addition is complete, methyl iodide (0.4 mole) is added, and the reaction mixture is stirred in the cold for two hours, then overnight at 25° C. The mixture is extracted with three 50 ml. portions of water and the organic phase is filtered and evaporated in vacuo to yield 2-benzoyl-7,8-dichloro-1-cyano-1-methyl-1,2-dihydroisoquinoline.

The 1-methyl compound prepared above (0.227 mole) 5 ml. of 95% ethanol and a solution of potassium hydroxide (0.57 mole) in 100 ml. of water are heated at reflux for 1.5 hours. The solution is cooled and extracted with ether. The extract is washed with water, dried over magnesium sulfate and evaporated to give, as the residue, 7,8-dichloro-1-methylisoquinoline.

By the procedure of Example 9, 7,8-dichloro-1-methyl-1,2,3,4-tetrahydroisoquinoline is prepared from 7,8-dichloro-1-methyl-isoquinoline.

Using ethyl iodide in place of methyl iodide in the above procedure, the product is 7,8-dichloro-1-ethyl-1,2,3,4-tetrahydroisoquinoline.

Alternatively, 7,8-dichloro-1-methylisoquinoline is prepared by the following procedure. 7,8-Dichloroisoquinoline (0.019 mole) in 100 ml. of dimethylsulfoxide is added to a solution of sodium hydride (0.11 mole) in 100 ml of dimethylsulfoxide at 70° C. The reaction mixture is stirred at 70° C. for four hours under a nitrogen atmosphere. The reaction mixture is cooled, 100 ml. of water is added, and the mixture is poured into 1500 ml. of water. The aqueous mixture is extracted with benzene. The extract is washed, dried over sodium sulfate and evaporated to give 7,8-dichloro-1-methylisoquinoline.

EXAMPLE 31

7,8-Dichloro-1,2,3,4-tetrahydroisoquinoline hydrochloride (0.001 mole) was treated with sodium acetate (0.001 mole), acetic anhydride (0.00125 mole), and 2 ml. of acetic acid and the mixture was heated at 95° C. for 15 minutes. The mixture was cooled, diluted with water, made alkaline with aqueous ammonia and extracted with chloroform. Concentration of the extract and recrystallization of the residue from isopropanol gave 2-acetyl-7,8-dichloro-1,2,3,4-tetrahydroisoquinoline, m.p. 99.5–100° C.

2-Acetyl-7,8-dichloro-1,2,3,4-tetrahydrisoquinoline is treated with excess diborane in tetrahydrofuran and refluxed for 16 hours. Methanol is added to destroy excess diborane and the solvent is removed in vacuo. The residue is dissolved in ether, treated with hydrogen chloride and filtered to give 7,8-dichloro-2-ethyl-1,2,3,4-tetrahydroisoquinoline hydrochloride.

EXAMPLE 32

7-Amino-8-chloro-1,2,3,4-tetrahydroisoquinoline is treated with one molar equivalent of isopropenyl acetate by the procedure of Example 15 to give 2-acetyl-7-amino-8-chloro-1,2,3,4-tetrahydroisoquinoline.

By the procedure of Example 24 the 7-amino group in the above prepared compound is converted to a 7-nitro group and the 2-acetyl group is removed by hydrolyzing in refluxing 10% hydrochloric acid by the procedure of Example 15 to give 8-chloro-7-nitro-1,2,3,4-tetrahydroisoquinoline.

Alternatively, a solution of peroxytrifluoroacetic acid is prepared from trifluoroacetic anhydride (0.24 mole) and 90% hydrogen peroxide (0.2 mole) in 100 ml. of methylene chloride cooled in an ice-bath. The resulting solution is stirred for five minutes and the cooling bath is removed. To this solution is added dropwise over a 30-minute period a solution of 7-amino-8-chloro-2-acetyl-1,2,3,4-tetrahydroisoquinoline (0.05 mole) in methylene chloride. After addition is complete, the solution is refluxed for one hour, cooled, and washed with 10% aqueous sodium carbonate solution. The methylene chloride phase is evaporated and the residue hydrolyzed in 10% hydrochloric acid as described above to give 8-chloro-7-nitro-1,2,3,4-tetrahydroisoquinoline.

EXAMPLE 33

2-Acetyl-8-amino-trifluoromethyl-1,2,3,4-tetrahydroisoquinoline, prepared as in Example 20, is converted to 2-acetyl-8-nitro-7-trifluoromethyl-1,2,3,4-tetrahydroisoquinoline by the procedure of Example 24. Removing the 2-acetyl group by acid hydrolysis according to the procedure of Example 15 gives 8-nitro-7-trifluoromethyl-1,2,3,4-tetrahydroisoquinoline.

EXAMPLE 34

7-Methoxy-β-methylphenethylamine and a 10% excess of formic acid are heated to 115° C. for three hours and the excess formic acid is then removed by distillation. Further distillation at ca. 200° C. and 0.05 mm. gives N-formyl-7-methoxy-β-methylphenethylamine. A mixture of 65 g. of phosphorous pentoxide and 235 g. of polyphosphoric acid at 170°–180° C. is stirred for one hour. The mixture is cooled to 150° C. and the above prepared N-formyl-7-methoxy-β-methylphenethylamine is added in portions. The mixture is stirred at 160°–170° C. for 1.5 hours, cooled slightly and poured into 500 ml. of water and ice. The mixture is extracted once with ether and then cooled and adjusted to pH 9 with aqueous potassium hydroxide solution. The product is extracted with ether and the extract is washed with water, dried over sodium sulfate and evaporated. The residue is distilled under vacuum. A mixture of 100 parts of the product and 25 parts of 10% palladium on charcoal in 200 ml. of p-cymene is refluxed for 1.5 hours. The catalyst is filtered off and the filtrate concentrated to 50 ml. and extracted with 10% hydrochloric acid. The extract is washed with chloroform, made basic with 10% aqueous potassium hydroxide solution and extracted with chloroform. The extract is evaporated to yield 7-methoxy-4-methylisoquinoline.

7-Methoxy-4-methylisoquinoline (0.02 mole) in 40 ml. of glacial acetic acid is stirred and cooled to 15° C. A solution of chlorine in cold glacial acetic acid is added until only 10% of the starting material remains. This requires 0.036 mole of chlorine in 26 ml. of acetic acid. The solvent is evaporated in vacuo nearly to dryness and the residue dissolved in 5% hydrochloric acid. The mixture is filtered and the filtrate basified with concentrated ammonium hydroxide and extracted with benzene. The extracts are washed with water, dried over sodium sulfate and evaporated. The 8-chloro-7-methoxy-4-methylisoquinoline is recrystallized from benzene-hexane.

8-Chloro-7-methoxy-4-methylisoquinoline (0.89 g.) in 48% hydrobromic acid is refluxed for 48 hours. The mixture is evaporated to dryness in vacuo, redissolved in water and neutralized with ammonium hydroxide. The mixture is cooled and the precipitate is filtered off and treated with hydrogen chloride in ethanol. Ether is added and the precipitate is filtered off to give 8-chloro-7-hydroxy-4-methylisoquinoline hydrochloride.

8-Chloro-7-hydroxy-4-methylisoquinoline (0.04 mole) and dichlorotriphenylphosphorane (0.04 mole) are heated to 240° C. under a nitrogen atmosphere. After four hours, the mixture is allowed to cool and is partitioned between chloroform and concentrated hydrochloric acid. The acidic extract is washed with chloroform, basified and extracted with chloroform. The chloroform extract is washed with water, dried over sodium sulfate and evaporated to yield 7,8-dichloro-4-methylisoquinoline. The product is purified by chromatography on silica gel eluted with chloroform and finally by precipitation of the hydrochloride from ethanol-ether.

Hydrogenation by the procedure of Example 9 gives 7,8-dichloro-4-methyl-1,2,3,4-tetrahydroisoquinoline.

EXAMPLE 35

Using 3-chloro-2-ethylbenzoic acid in place of 2-chloro-3-methylbenzoic acid in the procedure of Example 9 gives 7-chloro-8-ethyl-1,2,3,4-tetrahydroisoquinoline.

EXAMPLE 36

| Ingredients | Amounts |
| --- | --- |
| 7,8-Dichloro-1,2,3,4-tetrahydro-isoquinoline hydrochloride | 150 mg. |
| Lactose | 350 mg. |

The ingredients are mixed and filled into a hard gelatin capsule.

EXAMPLE 37

| Ingredients | Amounts |
| --- | --- |
| 7-Chloro-1,2,3,4-tetrahydro-isoquinoline | 200 mg. |
| Calcium sulfate dihydrate | 150 mg. |
| Sucrose | 25 mg. |
| Starch | 15 gm. |
| Talc | 5 mg. |
| Stearic acid | 3 mg. |

The calcium sulfate dihydrate, sucrose and 7-chloro-1,2,3,4-tetrahydroisoquinoline are thoroughly mixed and granulated with 10% gelatin solution. The wet granules are screened, dried and then mixed with the starch, talc and stearic acid, screened and compressed into a tablet.

| Ingredients | Amounts |
| --- | --- |
| 7-Nitro-1,2,3,4-tetrahydroisoquinoline | 150 mg. |
| Lactose | 100 mg. |
| Magnesium stearate | 5 mg. |

Similarly, tablets and capsules using 7-sulfamoyl-1,2,3,4-tetrahydroisoquinoline as the active ingredient are prepared according to the procedures of Examples 36–38.

What is claimed is:

1. A pharmaceutical composition to inhibit phenylethanolamine N-methyltransferase comprising a pharmaceutical carrier and, in an effective amount to inhibit phenylethanolamine N-methyltransferase, a tetrahydroisoquinoline compound of the formula:

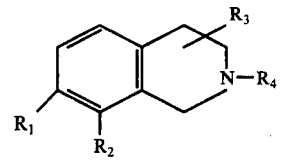

in which:
$R_1$ and $R_2$ are both trifluoromethyl or $R_1$ is sulfamoyl and $R_2$ is hydrogen
$R_3$ and $R_4$ are hydrogen or a pharmaceutically acceptable, acid addition salt thereof.

2. A pharmaceutical composition of claim 1 in which the tetrahydroisoquinoline compound is 7-sulfamoyl-1,2,3,4-tetrahydroisoquinoline.

3. A pharmaceutical composition of claim 1 in which the tetrahydroisoquinoline compound is 7,8-di-(trifluoromethyl)-1,2,3,4-tetrahydroisoquinoline.

4. A method of inhibiting phenylethanolamine N-methyltransferase which comprises administering to an animal, in an amount sufficient to inhibit phenylethanolamine N-methyltransferase, a tetrahydroisoquinoline compound of the formula:

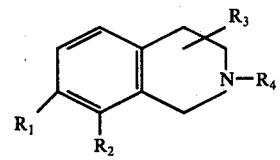

in which:
$R_1$ and $R_2$ are both trifluoromethyl or $R_1$ is sulfamoyl and $R_2$ is hydrogen and
$R_3$ and $R_4$ are hydrogen or a pharmaceutically acceptable, acid addition salt thereof.

5. A method of claim 4 in which the tetrahydroisoquinoline compound is 7-sulfamoyl-1,2,3,4-tetrahydroisoquinoline.

6. A method of claim 4 in which the tetrahydroisoquinoline compound is 7,8-di-(trifluoromethyl)-1,2,3,4-tetrahydroisoquinoline.

7. A method of reducing the formation of epinephrine in an animal under stress which comprises administering to said animal, in amount sufficient to reduce the formation of epinephrine, a tetrahydroisoquinoline compound of the formula:

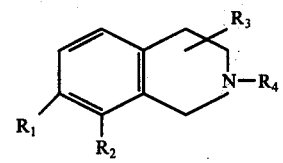

in which:
$R_1$ and $R_2$ are both trifluoromethyl or $R_1$ is sulfamoyl and $R_2$ is hydrogen and
$R_3$ and $R_4$ are hydrogen or a pharmaceutically acceptable, acid addition salt thereof.

8. A method of claim 7 in which the tetrahydroisoquinoline compound is 7-sulfamoyl-1,2,3,4-tetrahydroisoquinoline.

* * * * *

UNITED STATES PATENT AND TRADEMARK OFFICE
CERTIFICATE OF CORRECTION

PATENT NO. : 4,062,961
DATED : December 13, 1977
INVENTOR(S) : Carl Kaiser and Robert G. Pendleton It is certified that error appears in the above-identified patent and that said Letters Patent are hereby corrected as shown below:

Column 3, lines 15-25, the middle structure, that portion of the structure reading

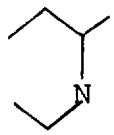   should read   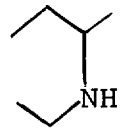

Signed and Sealed this

Second Day of May 1978

[SEAL]

Attest:

RUTH C. MASON
Attesting Officer

LUTRELLE F. PARKER
Acting Commissioner of Patents and Trademarks